US012721759B2

(12) United States Patent
Riha-Scott

(10) Patent No.: US 12,721,759 B2
(45) Date of Patent: Sep. 1, 2026

(54) MOISTURE RETAINING ARTICLE

(71) Applicant: RSD HOLDINGS LIMITED, Auckland (NZ)

(72) Inventor: Frantisek Riha-Scott, Auckland (NZ)

(73) Assignee: RSD HOLDINGS LIMITED, Auckland (NZ)

(*) Notice: Subject to any disclaimer, the term of this patent is extended or adjusted under 35 U.S.C. 154(b) by 398 days.

(21) Appl. No.: 17/777,889

(22) PCT Filed: Nov. 19, 2020

(86) PCT No.: PCT/IB2020/060882
§ 371 (c)(1),
(2) Date: May 18, 2022

(87) PCT Pub. No.: WO2021/099972
PCT Pub. Date: May 27, 2021

(65) Prior Publication Data

US 2023/0063486 A1 Mar. 2, 2023

(30) Foreign Application Priority Data

Nov. 19, 2019 (NZ) ........................................ 759341

(51) Int. Cl.
*A61F 13/14* (2006.01)
*A61F 13/15* (2006.01)
*A61F 13/45* (2006.01)

(52) U.S. Cl.
CPC ............ *A61F 13/45* (2013.01); *A61F 13/141* (2013.01); *A61F 13/15268* (2013.01); *A61F 2013/15016* (2013.01); *A61F 2013/15276* (2013.01)

(58) Field of Classification Search
CPC ................ A61F 13/45; A61F 13/15268; A61F 2013/15016; A61F 2013/15276;
(Continued)

(56) References Cited

U.S. PATENT DOCUMENTS 1,984,253 A 12/1934 Cox
1,989,382 A 1/1935 Schnaittacher
(Continued)

FOREIGN PATENT DOCUMENTS

CN 2193736 Y 4/1995
CN 207462236 U 6/2018
(Continued)

OTHER PUBLICATIONS

Extended European Search Report dated Sep. 21, 2023 for European Application No. 20889264.6.
(Continued)

*Primary Examiner* — Catharine L Anderson
(74) *Attorney, Agent, or Firm* — JCIP; Joseph G. Chu

(57) ABSTRACT

Disclosed is a moisture retaining article 1 of or for use with an undergarment to be positioned adjacent a person's body and to receive moisture from a person wearing the article 1. The article 1 comprises a leakproof assembly defined between an inner and an outer layer of leakproof flexible material There is a mouth entrance 12 to be presented to the person in a manner to allow moisture from the person to drain via the mouth entrance 12 into a leakproof pocket 10 of the leakproof assembly located below the mouth entrance 12.

20 Claims, 11 Drawing Sheets

(58) Field of Classification Search
CPC ...... A61F 5/4401; A61F 5/453; A61F 13/471; A61F 13/141
See application file for complete search history.

(56) References Cited

U.S. PATENT DOCUMENTS

| | | | | |
|---|---|---|---|---|
| 2,047,522 A | | 7/1936 | Schnaittacher | |
| 2,748,771 A | * | 6/1956 | Richards | A41C 3/04 450/36 |
| 5,149,336 A | | 9/1992 | Clarke et al. | |
| 5,326,305 A | * | 7/1994 | Fochler | A61F 13/145 450/55 |
| 5,435,014 A | | 7/1995 | Moretz et al. | |
| 6,074,272 A | * | 6/2000 | Hebert | A61F 13/141 450/37 |
| 6,129,718 A | * | 10/2000 | Wada | A61F 13/471 604/385.03 |
| 6,695,678 B1 | * | 2/2004 | Foley | A61F 13/141 450/57 |
| 8,708,771 B1 | | 4/2014 | De Rosa | |
| 2003/0211810 A1 | | 11/2003 | Raimondo | |
| 2005/0015067 A1 | * | 1/2005 | Suzuki | A61F 13/551 604/385.02 |
| 2006/0106355 A1 | * | 5/2006 | Bruce | A61F 13/141 604/385.07 |
| 2014/0364825 A1 | * | 12/2014 | Krasikoff | A61F 13/145 604/385.03 |
| 2015/0335497 A1 | * | 11/2015 | Montford | A61F 13/141 604/385.14 |
| 2018/0168872 A1 | * | 6/2018 | Madden | A61F 13/515 |

FOREIGN PATENT DOCUMENTS

| | | |
|---|---|---|
| CN | 209172701 U | 7/2019 |
| EP | 0619953 A1 | 10/1994 |
| EP | 2604236 B1 | 11/2016 |

OTHER PUBLICATIONS

International Search Report and Written Opinion of the International Searching Authority dated Feb. 1, 2021 for International Application No. PCT/IB2020/060882.

International Preliminary Report on Patentability dated Mar. 11, 2022 for International Application No. PCT/IB2020/060882.

First Office Action dated Dec. 31, 2024 for Chinese Application No. 202080080142.7.

Examination Report 1 dated Oct. 22, 2025 from New Zealand Intellectual Property Office for Application No. NZ770055.

* cited by examiner

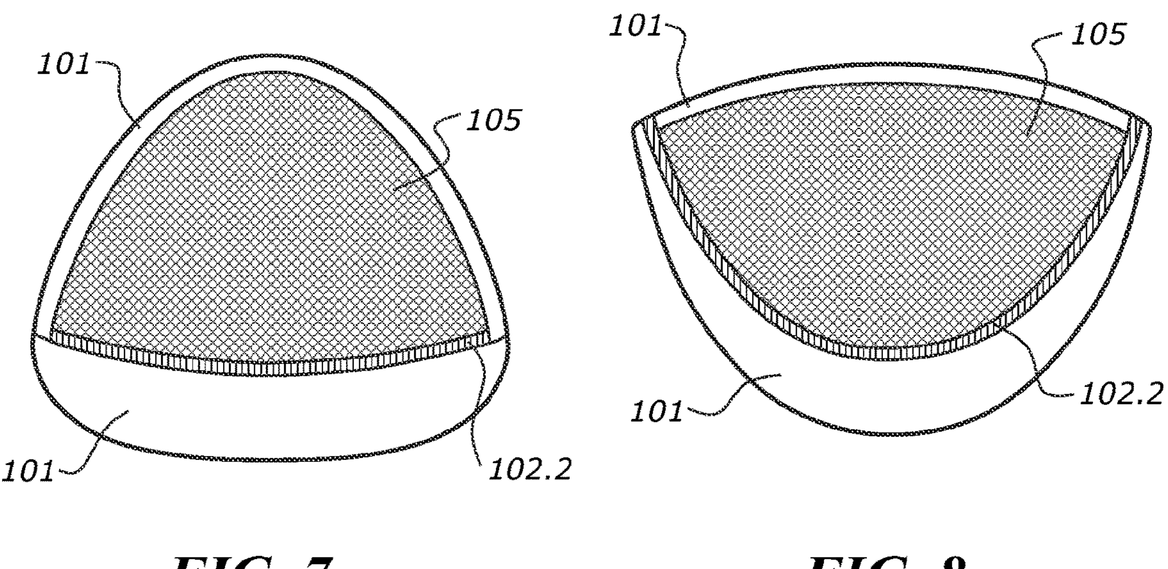
FIG. 7
FIG. 8
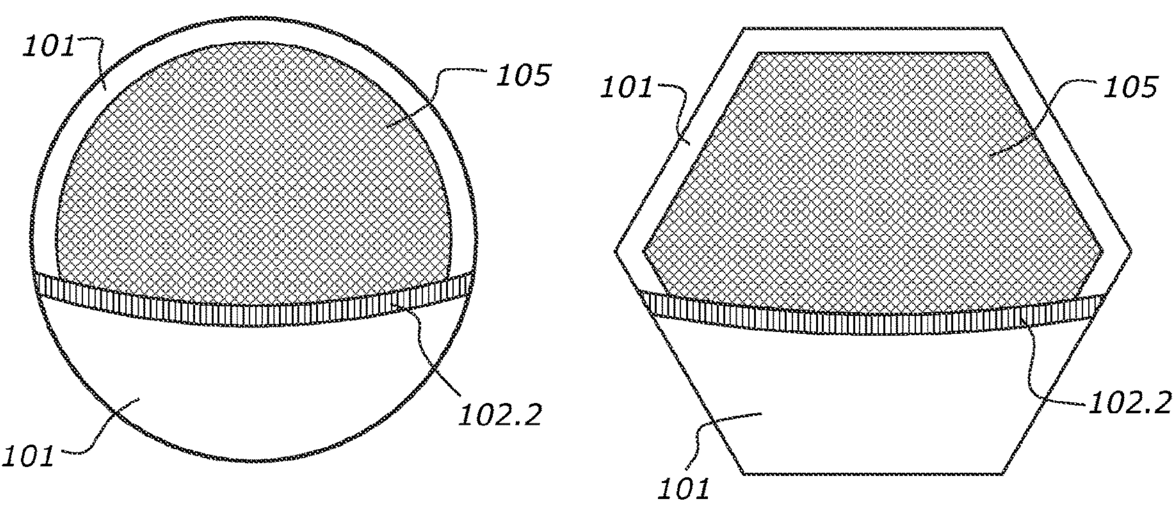
FIG. 9
FIG. 10

MOISTURE RETAINING ARTICLE

FIELD OF INVENTION

The present invention relates to a moisture retaining article, and in particular but not exclusively to a nursing pad assembly or urinal pouch assembly for men or woman that may form part of or be used with undergarments to be worn by a person.

BACKGROUND

Moisture retaining articles such as nursing pads are known. They may be placed intermediate of a nipple and a breast cup of a bra. Some bras incorporate such pads. However, such pads have a limited capacity for holding breast milk.

Their capacity is determined by the absorbency of the materials used in the pad. Due to the limited capacity, during use, the breast milk can easily leak from the pad thereby defeating its purpose.

OBJECT OF THE INVENTION

It is therefore be an object of the present invention to provide a moisture retaining article that provides enhanced moisture retention beyond the absorbency of the materials of the article and/or that will at least provide the public with a useful choice.

BRIEF DESCRIPTION OF THE INVENTION

Accordingly in a first aspect the present invention may be said to be a moisture retaining article of or for use with an undergarment to be positioned adjacent a person's body and to receive moisture from a person wearing the article, the article comprising:

a. a leakproof layer formed or assembled to define, at an upper region of the article, an outer layer of the article and, at a lower region of the article, an outer layer and an inner layer of the article, a leakproof pocket formed between the inner and outer layer at the lower region to allow moisture received from the person, to drain under gravity into the leakproof pocket.

Preferably the article is positioned to receive moisture from the person from above the leakproof pocket.

Preferably the article is positioned with the inner layer more proximate the person than the outer layer at the lower region.

Preferably the leakproof pocket is formed by and between the inner and outer layer at the lower region to allow moisture to drain under gravity into the leakproof pocket.

Preferably the leakproof pocket is formed between the inner and outer layer at the lower region to allow moisture received from the person, to drain under gravity into the leakproof pocket and be retained in the leakproof pocket when the article is in its upright condition with the upper region above the lower region.

Preferably the leakproof layer extends downwardly from the upper region to the bottom of the lower region at its outer layer and extends upwardly from the bottom of the lower region to the top of the lower region at its inner layer.

Preferably the leakproof layer extends downwardly from the top of the upper region to the bottom of the lower region at its outer layer and extends upwardly from the bottom of the lower region to the top of the lower region at its inner layer.

Preferably the leakproof layer extends downwardly from the top of the upper region to the bottom of the lower region at its outer layer and extends upwardly from the bottom of the lower region no higher than the top of the lower region at its inner layer.

Preferably a window to receive moisture by the article is defined between the top of the leakproof layer at the inner layer and the top of the leakproof layer at the top of the outer layer, preferably at the outer layer at the upper region.

Preferably a mouth entrance to the leakproof pocket is defined between the top of the leakproof layer at the inner layer and the outer layer, preferably the outer layer at the lower region.

Preferably a mouth entrance is the only opening to the leakproof pocket.

Preferably the mouth entrance is the upper most part of the leakproof pocket.

Preferably the leakproof pocket is defined by the outer layer and inner layer of the leakproof layer peripherally bonded to each other save for at the mouth entrance.

Preferably an outer more layer is located outwardly of the outer layer.

Preferably an outer more layer is located outwardly of the outer layer at at least one of the upper and lower regions.

Preferably the outer more layer is the outer most layer of the article.

Preferably the outer more layer is a decorative layer of the article.

Preferably the outer more layer is a protective layer to the outer layer.

Preferably the outer more layer is a protective layer to the outer layer at at least one of the upper and lower regions.

Preferably the outer more layer is laminated or otherwise bonded to the outer layer.

Preferably the outer more layer is laminated or otherwise bonded to the outer layer using adhesive and heat bonding.

Preferably the outer more layer is laminated or otherwise bonded to the outer layer at at least one of the upper and lower regions, preferably using adhesive and heat bonding. Preferably the outer more layer is coextensive with the outer layer.

Preferably the outer more layer is coextensive with the outer layer at at least one of the upper and lower regions.

Preferably the outer more layer extends from the top of the article to the bottom of the article.

Preferably, the outer more layer comprises one or more anti-slip prints at outermost surface.

Preferably, one or more anti-slip prints are rubber prints.

Preferably, the anti-slip prints are made out of a silicon material.

Preferably, the silicon material glows in the dark.

Preferably an inner more layer is located outwardly of the inner layer.

Preferably the inner more layer is an inner most layer of the article.

Preferably the inner more layer is a decorative layer of the article.

Preferably the inner more layer is a protective layer to the inner layer.

Preferably the inner more layer is laminated or otherwise bonded to the inner layer.

Preferably the inner more layer is laminated or otherwise bonded to the inner layer using adhesive and heat bonding.

Preferably the inner more layer is coextensive with the inner layer.

Preferably the inner more layer extends from the top of the lower region of article to the bottom of the article.

Preferably the inner more layer extends from the mouth entrance of the leakproof pocket to the bottom of the article.

Preferably a core is provided located at least in the leakproof pocket.

Preferably is the leakproof pocket is filled with a core. Preferably a core is provided located to the inside of the outer layer.

Preferably a core is provided located to the inside of the outer layer at at least one of the upper and lower regions.

Preferably a core provided located to the outside of the inner layer.

Preferably a core is provided laminated or otherwise bonded to at least one of the outer layer and inner layer, preferably the outer layer being the outer layer at at least one of the upper and lower regions.

Preferably a core is provided comprising of a multi layer assembly of at least two of:

a. a wicking layer, b. a moisture absorbing layer, and c. a foam layer.

Preferably, at least two of the wicking layer, the moisture absorbing layer and the foam layer are stitched together around their edges (preferably up to 2 mm from their edges) to form a stitched assembly.

Preferably, the outer more layer and inner more layer may be bonded to the stitched assembly using adhesive and heat bonding process.

Preferably the wicking layer is the inner most layer at the upper region of the article.

Preferably the wicking layer is presented for contact with the wearer.

Preferably the wicking layer is presented for contact with the wearer at the window and/or the mouth entrance.

Preferably the wicking layer extends from the top of the article to the bottom of the article and in the leakproof pocket.

Preferably the wicking layer extends from the top of the article to the bottom of the article and in the leakproof pocket where it is laminated or otherwise bonded to the inner layer.

Preferably the moisture absorbing layer is located adjacent the wicking layer and is preferably laminated or otherwise bonded to the wicking layer.

Preferably the moisture absorbing layer is located adjacent the wicking layer and is preferably laminated or otherwise bonded to the outer layer.

Preferably the moisture absorbing layer is located adjacent the wicking layer and is preferably laminated or otherwise bonded to the outer layer at at least one of the upper and lower regions.

Preferably the moisture absorbing layer is located adjacent the wicking layer and is preferably laminated or otherwise bonded to the wicking layer and is preferably laminated or otherwise bonded to the outer layer.

Preferably the moisture absorbing layer is located adjacent the wicking layer and is preferably laminated or otherwise bonded to the wicking layer and is preferably laminated or otherwise bonded to the outer layer at at least one of the upper and lower regions.

Preferably the moisture absorbing layer extends from the top of the article to the bottom of the article and in the leakproof pocket.

Preferably the foam layer is located adjacent the moisture absorbing layer and is preferably laminated or otherwise bonded to the moisture absorbing layer.

Preferably the foam layer extends from the top of the article to the bottom of the article and in the leakproof pocket.

Preferably the foam layer is shaped in thickness. Preferably the foam layer is of uneven thickness.

Preferably the moisture absorbing layer is shaped in thickness.

Preferably the moisture absorbing layer is of uneven thickness.

Preferably the article is presented as multilayer assembly.

Preferably the article is presented as multilayer assembly of laminated layers of material.

Preferably the article is presented as a pad of a multilayer assembly.

Preferably the article is of a contoured shape.

Preferably the article is a nursing pad.

Preferably the article is a nursing pad configured to be positioned adjacent a person's breast for receiving moisture from the person's breast.

Preferably the article is an incontinence pouch for men that is configured to be positions adjacent a person's genital for receiving moisture from genital area of the person.

In a second aspect the present invention may broadly be said to be a garment that includes said article as herein described.

Preferably the garment is able to receive the article in a dedicated location of the garment.

In a further aspect the present invention may be said to be a moisture retaining article of or for use with an undergarment to be positioned adjacent a person's body and to receive moisture from a person wearing the article, the article comprising a leakproof assembly defined between an inner and an outer layer of leakproof flexible material the article or the inner layer having a window opening to be presented to the person in a manner to allow moisture from the person to drain via the window opening into a leakproof pocket or leakproof pocket region of the leakproof assembly located below the window opening.

In a further aspect the present invention may be said to be a moisture retaining article of or for use with an undergarment to be positioned adjacent a person's body and to receive moisture from a person wearing the article, the article comprising a leakproof assembly defined between an inner and an outer layer of leakproof flexible material the article or the inner layer having a mouth entrance to be presented to the person in a manner to allow moisture from the person to drain via the mouth entrance into a leakproof pocket or leakproof pocket region of the leakproof assembly located below the mouth entrance.

In a further aspect the present invention may be said to be a moisture retaining article of or for use with an undergarment to be positioned adjacent a person's body and to receive moisture from a person wearing the article, the article comprising a leakproof assembly defined between an inner layer and an outer layer of leakproof flexible material, the leakproof assembly having a mouth entrance to be presented to the person in a manner to allow moisture from the person to drain via the mouth entrance into a leakproof pocket or a leakproof pocket region of the leakproof assembly located below the mouth entrance.

In a further aspect the present invention may be said to be a moisture retaining article to be positioned adjacent a person's body and to receive moisture from the person, the article having an inside face and outside face and comprising a multi-layer assembly of a leakproof layer or assembly of layers defining a leakproof pouch below a collection region, the collection region including a window opening of the leakproof layer or assembly of layers at the inside face at where there is presented a porous layer or layers of material able to receive, via the window opening, moisture from the person to drain under gravity into and for pooling in the pouch.

Preferably the leakproof layer or assembly of layers is provided to prevent transfer of moisture through the outside face of the article.

Preferably the leakproof layer or assembly of layers cover porous layer or layers to the outside of the porous layer or layers.

Thus, in one aspect the present invention may be said to be a moisture retaining article of or for use with an undergarment to be positioned adjacent a body of a person wearing the article and to receive moisture from the person wearing the article, the article comprising:

a leakproof layer that is formed or assembled to define an outer layer of the article at an upper region of the article, and an outer layer (which is a further outer layer) and an inner layer of the article at a lower region of the article; and a leakproof pocket that is formed between the inner and outer layer at the lower region to allow moisture received from the person, to drain under gravity into the leakproof pocket.

Thus, in a further aspect the present invention may be said to be a moisture retaining article of or for use with an undergarment to be positioned adjacent a body of a person wearing the article and to receive moisture from the person, the article comprising a leakproof assembly defined between an inner layer and an outer layer of leakproof flexible material, the article or the inner layer having a window opening to be presented to the person in a manner to allow moisture from the person to drain via the window opening into a leakproof pocket or a leakproof pocket region of the leakproof assembly located below the window opening.

Thus, in a further aspect the present invention may be said to be a moisture retaining article of or for use with an undergarment to be positioned adjacent a body of a person wearing the article and to receive moisture from the person, the article comprising a leakproof assembly defined between an inner and an outer layer of leakproof flexible material, the article or the inner layer having a mouth entrance to be presented to the person in a manner to allow moisture from the person to drain via the mouth entrance into a leakproof pocket or a leakproof pocket region of the leakproof assembly located below the mouth entrance.

Thus, in a further aspect the present invention may be said to be a moisture retaining article of or for use with an undergarment to be positioned adjacent a body of a person wearing the article and to receive moisture from the person, the article comprising a leakproof assembly defined between an inner layer and an outer layer of leakproof flexible material, the leakproof assembly having a mouth entrance to be presented to the person in a manner to allow moisture from the person to drain via the mouth entrance into a leakproof pocket region of the leakproof assembly located below the mouth entrance.

Thus, in a further aspect the present invention may be said to be a moisture retaining article to be positioned adjacent a body of a person wearing the article and to receive moisture from the person wearing the article, the article having an inside face and outside face and comprising a multi-layer assembly of a leakproof layer or assembly of layers defining a leakproof pouch below a collection region, the collection region including a window opening of the leakproof layer or assembly of layers at the inside face at where there is presented a porous layer or layers of material able to receive, via the window opening, moisture from the person to drain under gravity into and for pooling in the pouch.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

Unless stated otherwise the term "leakproof" may include "completely leakproof" or "substantially leakproof".

The entire disclosures of all applications, patents and publications, cited above and below, if any, are hereby incorporated by reference.

BRIEF DESCRIPTION OF THE DRAWINGS

The invention will now be described by way of example only and with reference to the drawings in which:

FIGS. 7-10 represent various design shapes of the nursing pad assembly with the leakproof and fully sealed gravity moisture collection pocket.

DETAILED DESCRIPTION

Preferred forms of the present invention will now be described with reference to the figures attached.

Figure 2:
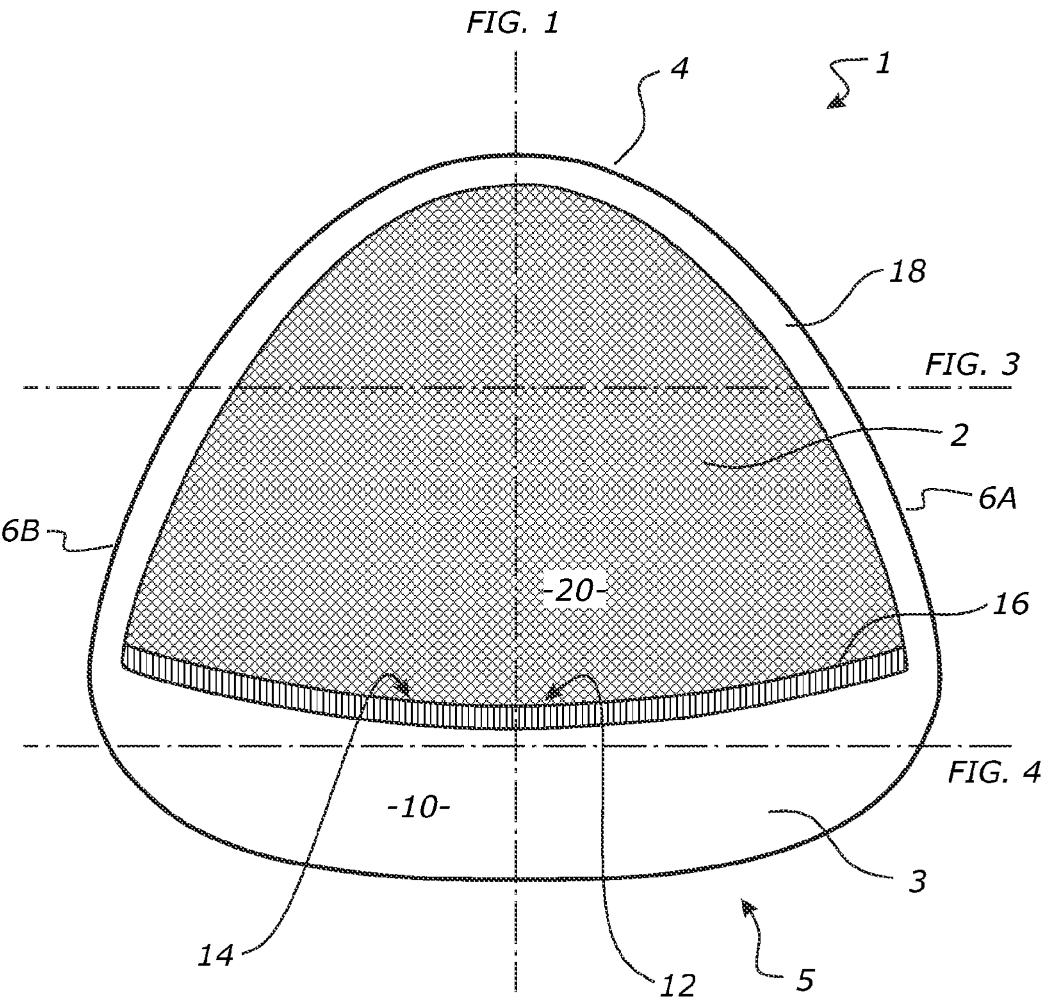
FIG. 2 shows a rear view nursing pad with cut through positions for FIGS. 1, 3 and 4.
Figure 2A:
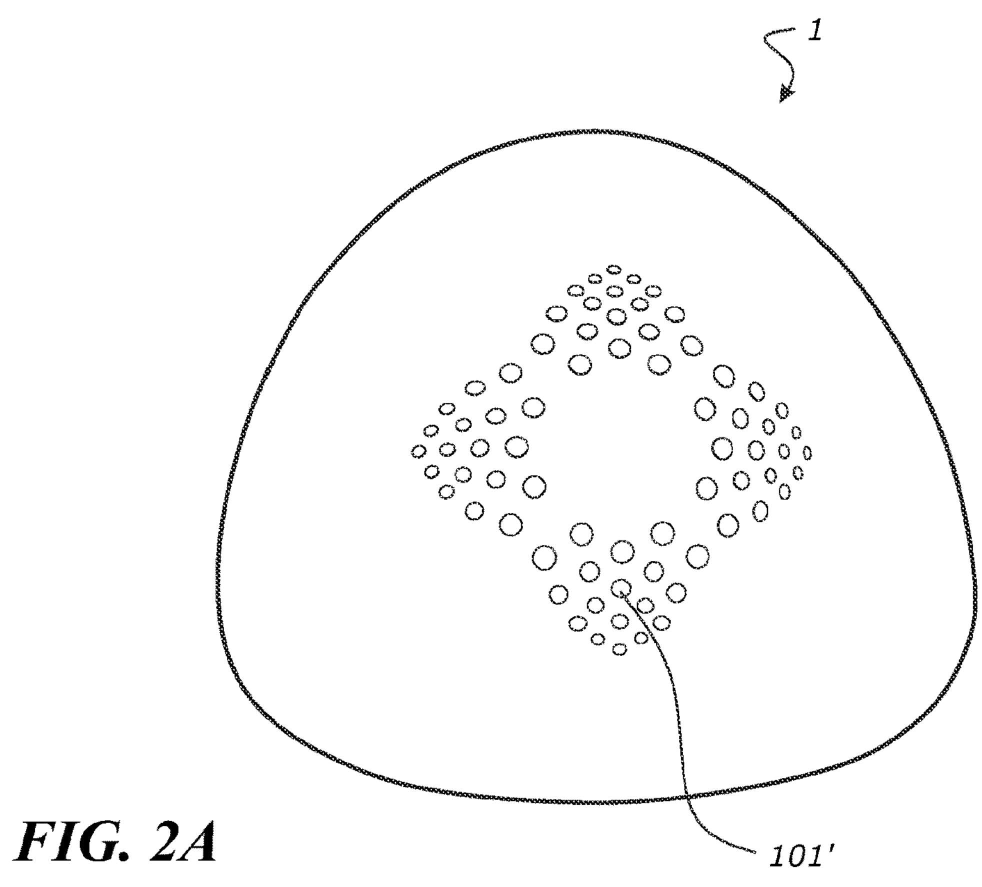
FIG. 2A shows a front view of the nursing pad of FIG. 2.

FIG. 2 shows a rear view (looking onto the inner side) of a moisture retaining article. The moisture retaining article is in this example a nursing pad 1. The article may be of or for use with an undergarment 500 to be positioned adjacent a person's body and to receive moisture from a person 80 wearing the article. Inner side may be the side that is proximal to the person's body and faces towards the person's body during use and outer side may be the side that is distal from the person's body and faces away from the person's body during use.

The nursing pad 1 comprises an upper region 2 and a lower region 3. It also comprises a top 4 and a bottom 5 extending between which are lateral sides 6*a* and 6*b*.

Figure 1:
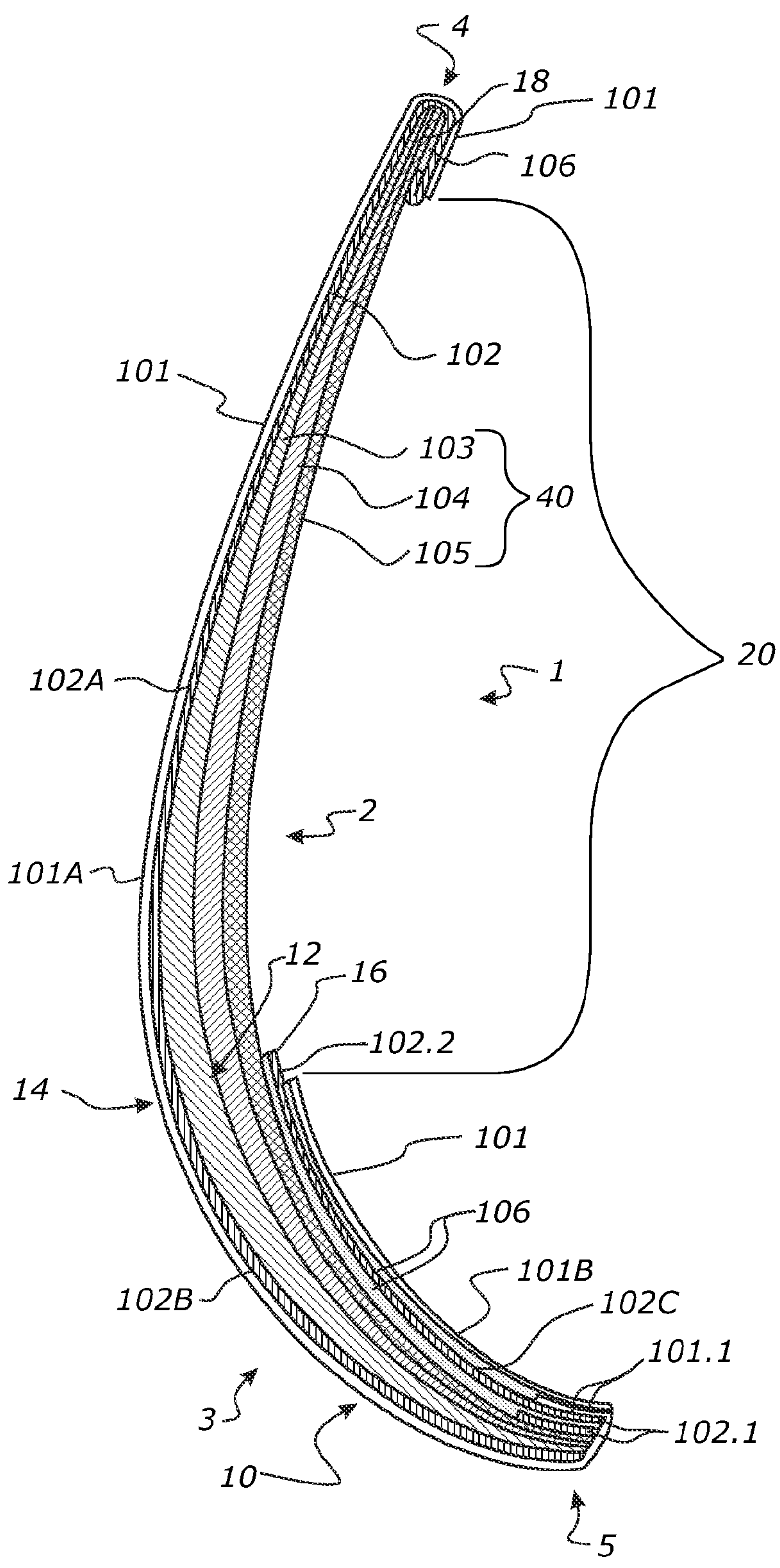
FIG. 1 is a cut through view of a gravity moisture collection assembly in the form of nursing pad assembly defining a gravity moisture collection pocket and other textile layers utilized.

FIG. 1 is a cut through view of FIG. 2 to show more detail. In the preferred form the nursing pad 1 comprises a leakproof layer 102, formed or assembled to define, at an upper region 2 of the article an outer layer 102A and at a lower region 3 of the article, an outer layer 102B and an inner layer 102C of the article creating a leakproof pocket 10 formed between the inner layer 102C and outer layer 102B at the lower region 3. This allows moisture received from the person at the inner side of the upper region 2, to drain under gravity into the leakproof pocket 10. The outer layer 102B and 102A are preferably continuous. It may be made from one ply of material such material being leakproof. The inner layer 102C is preferably sealingly engaged to the outer layer 102B at the bottom 5 and peripheral sides 6A and 6B to define a leakproof pocket 10. This sealing can be seen at region 102.1 and may be facilitated in a partial overlap between the inner layer 102C and the outer layer 102B and the use of an adhesive or heat welding to bond the layers there together.

Between the inner layer 102C and the outer layer 102B a pocket is so formed that is leakproof and can receive moisture from above via a mouth opening mouth entrance 12 of the leakproof pocket 10. The leakproof pocket 10 is substantially and preferably entirely filled with a core that will herein after be explained. The leakproof layer at the inner layer preferably finishes above the inner most layer at 102.2 so as to help prevent the inner most layer from absorbing moisture from the wicking layer. The inner layer 102C is hence preferably obscured from view by the inner more layer 101B except for the strip 102.2 the protrudes above the top edge of the inner layer 102C.

The article is able to be positioned relative a person to receive moisture from the person from above the leakproof pocket 10. The article in use is able to be positioned with the inner layer 102C more proximate the person than the outer layer 102B at the lower region 3.

Figure 6:
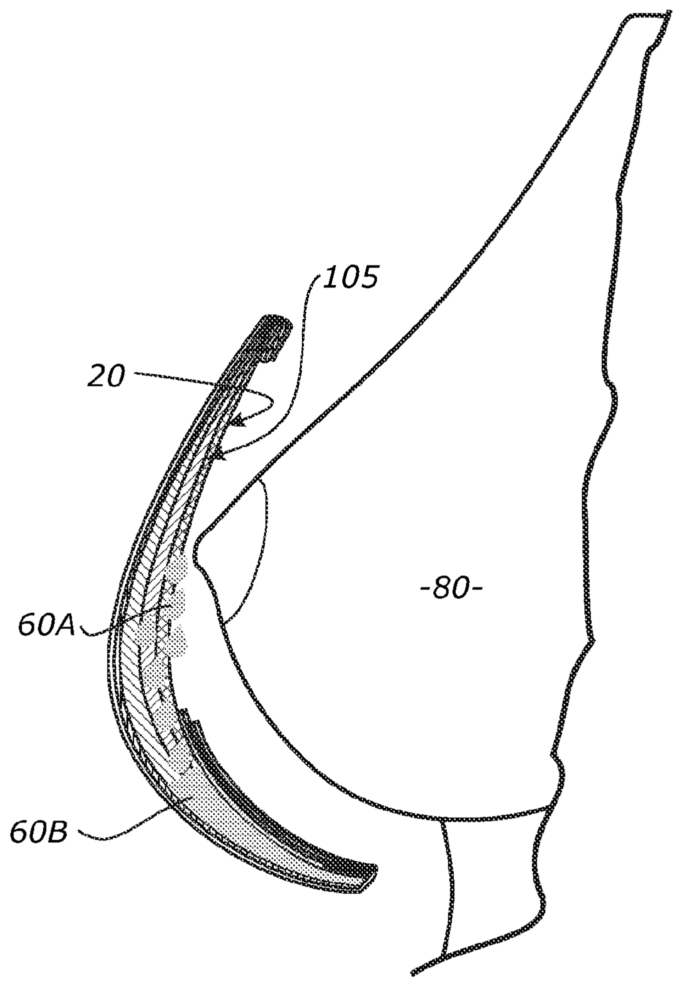
FIG. 6 represents a nursing pad assembly and breast milk absorption direction with moisture collection at the lower part of the gravity moisture collection pocket of the nursing pad assembly.

This can be seen in FIG. 6. The moisture can drain into the pocket via the mouth entrance 12 of the pocket 10, reliant on gravity. The mouth entrance 12 is located at the top 14 of the pocket 10. The leakproof pocket 10 is formed by and between the inner layer 102C and outer layer 102B at the lower region 3 to allow moisture to drain under gravity into the leakproof pocket 10. The leakproof pocket is formed between the inner and outer layer at the lower region to allow moisture received from the person, to drain under gravity into the leakproof pocket 10 and be retained in the leakproof pocket 10 when the article is in its upright condition with the upper region above the lower region. The height of the leakproof pocket 10 may be higher or lower than what is shown in FIG. 2.

The leakproof layer 102 preferably extends downwardly from the upper region 2 to the bottom 5 of the lower region 3 at its outer layer 102A/B and extends upwardly from the bottom 5 of the lower region 3 to the top 16 of the bottom/lower region 3 at its inner layer 102C. A hem 18 may form part of the outer layer 102A/B that extends around to the inner side. The leakproof layer preferably extends downwardly from the top 4 of the upper region 2 to the bottom 5 of the lower region 3 at its outer layer and extends upwardly from the bottom 5 of the lower region 3 to the top 16 of the bottom/lower region at its inner layer. Preferably the leakproof layer extends upwardly from the bottom 5 of the lower region 3 no higher than the top 16 of the bottom/lower region 3 at its inner layer 102C.

A window region 20 (or window opening 20 or window 20) is defined at the inner side of the nursing pad 1. This window region 20 is where moisture is received by the pad. The window region 20 may be defined between the top 16 of the leakproof layer at the inner layer and the top 4 of the leakproof layer at the top 4 of the outer layer 102A. It may be defined between the lateral sides 6A and 6B. The mouth entrance 12 to the leakproof pocket 10 is defined between the top 16 of the leakproof layer at the inner layer 102 C and the outer layer 102B and it is via the mouth entrance 12 that moisture can drain from above. The mouth entrance 12 is preferably the only opening to the leakproof pocket 10. The mouth entrance 12 is preferably the upper most part of the leakproof pocket. The leakproof pocket 10 is defined by the outer layer and inner layer of the leakproof layer peripherally bonded to each other save for at the mouth entrance 12.

In a preferred form there is an outer more layer 101A that is located outwardly of the outer layer 201A/B. The outer more layer 101A is preferably the outer most layer of the article. The outer more layer is preferably a decorative layer of the article. The outer more layer 101A is preferably a protective layer to the outer layer. The outer more layer 101A is preferably laminated or otherwise bonded to the outer layer. This may be achieved by the use of adhesive and/or heat bonding. The outer more layer preferably is coextensive with the outer layer. It may also include a hem region 18. It may also fold around the bottom of the pad. Preferably the outer more layer extends from the top of the article to the bottom of the article. Preferably, the outer more layer 101A comprises anti-slip prints 101' (e.g. anti-slip rubber prints) at outermost surface to avoid movements when the nursing pad 1 is placed inside an undergarment such as bra. In certain embodiments, the anti-slip prints 101' may be made out of a silicon material, preferably silicon material that glows in the dark.

There may also be provided an inner more layer 101B that is located outwardly of the inner layer 102C. The inner more layer is preferably an inner most layer of the article at the inner side of the pad 1. The inner more layer 102B may be a decorative layer of the article. The inner more layer may be a protective layer to the inner layer. The inner more layer 1016 faces towards the person's body during use.

Preferably the inner more layer 1016 is laminated or otherwise bonded to the inner layer. This may be achieved by the use of an adhesive and/or heat bonding. The inner more layer 1016 is preferably coextensive with the inner layer.

The inner more layer 1016 preferably extends from the top 16 of the bottom/lower region 3 of the article to the bottom 5 of the article. The inner more layer 1016 preferably extends from the mouth region/mouth entrance 12 of pocket 10 to the bottom 5 of the article.

Preferably a core 40 is provided located at least in the pocket. The core 40 is preferably a layer or layers of material of a porous nature. The core 40 helps hold the mouth entrance 12 open so that the two outer layers 102B and 102C cannot contact each other at the mouth entrance 12. This allow for moisture to drain into the leakproof pocket 40. The core 40 extends across the entire mouth entrance. The core 40 is substantially porous so as to all moisture to drain therethrough. The leakproof pocket 40 is hence preferably not able to be access through the mouth entrance other than by fluid transferring through the core 40, including the moisture transferring through the core 40.

Preferably the entire pocket is filled by the core 40. Preferably the core 40 is provided and located to the inside (inner side) of the outer layer 102B and preferably 102A. Preferably the core 40 provided located to the outside (outer side) of the inner layer 102C. In the preferred form the core is provided laminated or otherwise bonded to at least one of the outer and inner layer. The core 40 as well as providing the function to keep the mouth entrance one also may have additional functions. The core is preferably provided comprising of a multi-layer assembly of at least two of:

a. a wicking layer 105, b. a moisture absorbing layer 104, and c. a foam layer 103.

The foam layer 103 may be optional. Preferably the wicking layer 105 is the inner most layer at the upper region of the article. Preferably the wicking layer 105 is presented for contact with the wearer at the window region. This can be seen in FIG. 6 where moisture such as breast milk 60A is able to contact the wicking layer and thereby be captured by the pad. Under the influence of gravity the moisture drains down and into the pocket 10 where a pool 60B of moisture may collect. The wicking layer 105 preferably extends from the top 4 of the article to the bottom 5 of the article and in the leakproof pocket 10. The wicking layer 105 preferably extends from the top 4 of the article to the bottom 5 of the article and in the leakproof pocket where it is laminated or otherwise bonded to the inner layer 102C. Preferably the moisture absorbing layer 104 is located adjacent the wicking layer 105 and is preferably laminated or otherwise bonded to the wicking layer 105. The moisture absorbing layer 104 is preferably located adjacent the wicking layer 105 and is preferably laminated or otherwise bonded to the outer layer 102A/B.

The moisture absorbing layer 104 may be located adjacent the wicking layer 105 and is preferably laminated or otherwise bonded to the wicking layer 105 and is preferably laminated or otherwise bonded to the outer layer.

Preferably the moisture absorbing layer 104 extends from the top 4 of the article to the bottom 5 of the article and in the leakproof pocket 10.

Preferably the foam layer 103 is located adjacent the moisture absorbing layer 104 and is preferably laminated or otherwise bonded to the moisture absorbing layer 104. The foam layer 103 may extend from the top 4 of the article to the bottom 5 of the article and in the leakproof pocket 10.

The foam layer 103 is preferably shaped in thickness and may hence be of uneven thickness. The moisture absorbing layer 104 may also be so shaped in thickness to be of an uneven thickness. They may be shaped under high temperature to hold the shape of the nursing pad.

The moisture absorbing layer 104 may be made from chipped microfibre with a high fibre surface to collect any moisture.

The wicking layer 105 may be a textile that is designed to wick moisture away from the discharge point and transfer into the moisture absorbing layer 104.

Bonding tapes 106 may be used that seal with layers of the pad at high temperatures together without the need to use a stitch to remain 100% leakproof. Such may be made out of plant oil. 101.1 shows layer seal of the outer textile and 102.2 shows leakproof textile finishing above outer layer 101/external article layer 101 to help prevent any moisture absorption by layer 101.

In certain embodiments, at least the moisture absorbing layer 104 and the wicking layer 105 (and optionally the foam layer 105) are stitched together around the edge (e.g. up to 2 mm from the edge). The stitched layers may then be bonded to the inner layer 102C and outer layers 102A and 102B (or bonded to the leak proof layer 102) using adhesive and heat bonding process, thereby minimising the stitching required. The outer more layer 101A and inner more layer 101B may be bonded to the inner layer 102C and outer layers 102A and 102B (or bonded to the leakproof layer 102) using adhesive and heat bonding process.

In certain embodiments, at least the moisture absorbing layer 104, the wicking layer 105, the foam layer 105 (if present), the inner layer 102C and outer layers 102A and 102B are stitched together are stitched together around the edge (e.g. up to 2 mm from the edge) to form a stitched assembly. The outer more layer 101A and inner more layer 101B may be bonded to the stitched assembly using adhesive and heat bonding process.

The pad may present itself as multilayer assembly such as of a multilayer assembly of laminated layers of material. The pad may be provided as contoured shape.

Figure 3:
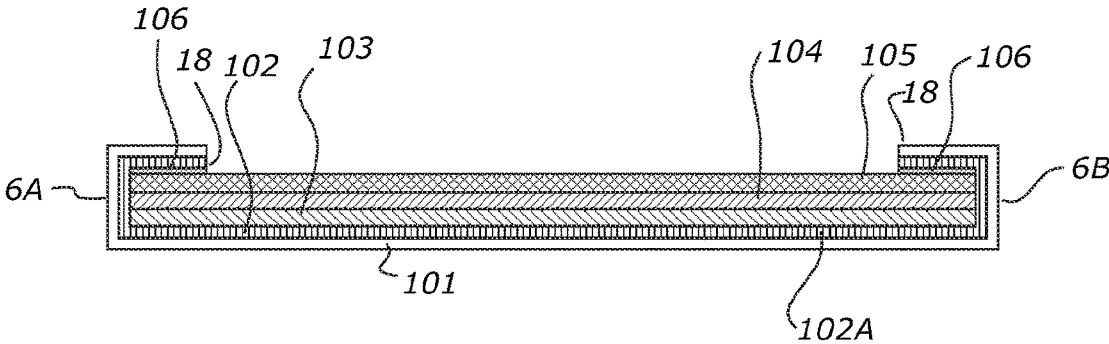
FIG. 3 is a cut through view of the nurse pad assembly at the higher moisture absorbing section, namely at the first point of breast milk discharge.
Figure 4:
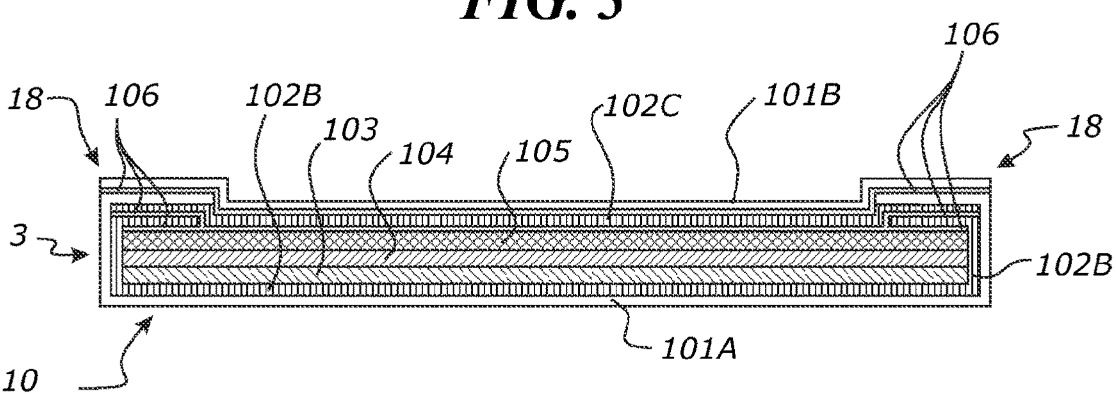
FIG. 4 is a cut through view of the nurse pad assembly at the lower section that is fully leakproof all around and is the gravity pocket that collects all moisture and retains it within the pocket

FIG. 3 is a cut through view of the nurse pad assembly at the higher moisture absorbing window, namely at the first point of breast milk discharge. FIG. 4 is a cut through view of the nurse pad assembly at the lower section that is fully leakproof all around and is the pocket that collects moisture and retains it within the pocket.

Figure 5:
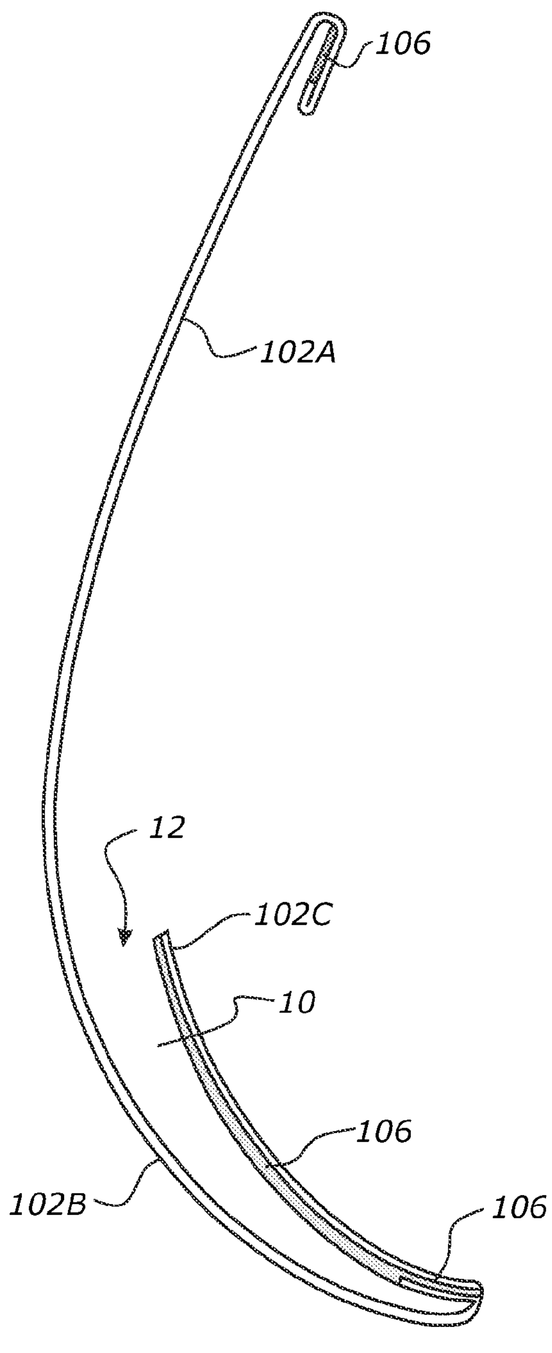
FIG. 5 is a cut through view of the leakproof layer of the nursing pad assembly at the gravity moisture collection pocket.

FIG. 5 is a cut through view of the leak proof layer of the nursing pad.

The nursing pad may not necessarily look like the one as shown in FIG. 2. FIGS. 7-10 represent various other design shapes of the nursing pad according to the present invention with the leakproof and fully sealed gravity moisture collection pocket. In FIGS. 7-10 same reference numerals as used in FIGS. 1-6 have been used to indicate corresponding features.

FIGS. 11-16 show moisture retaining article in the form of a men's pouch 1 which is an incontinence pouch for men. FIG. 17 shows a front view of an undergarment in the form of underpants that include or can incorporate the men's pouch of FIGS. 11-16. In FIGS. 11-17 same reference numerals as used in FIGS. 1-6 have been used to indicate corresponding features. In certain embodiments, the layers may be bonded using stitches and adhesive and heat bonding process in a similar manner as described above.

Figure 11:
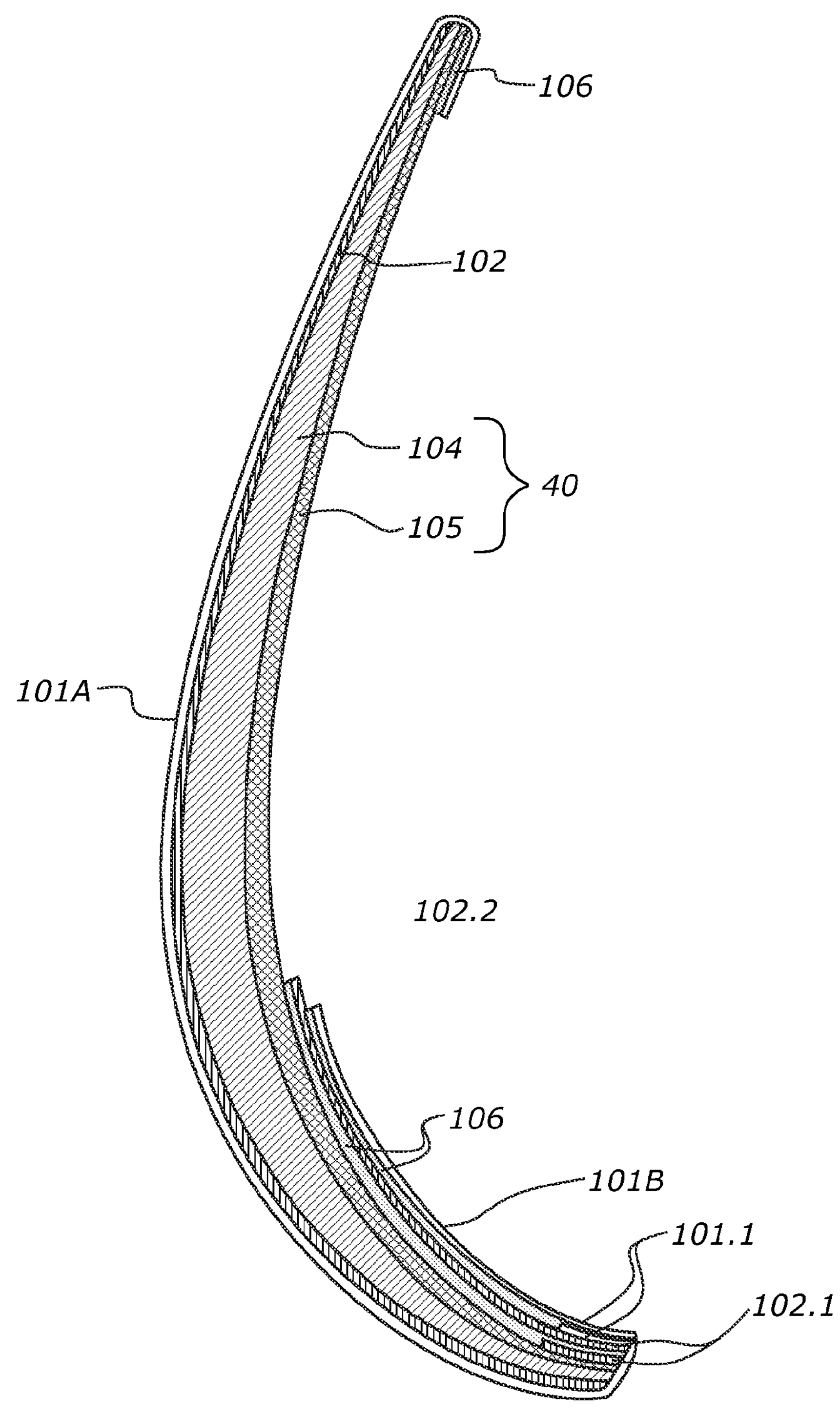
FIG. 11 represents a cut through of a gravity moisture collection assembly in the form of a mens pouch assembly with a gravity moisture collection pocket
Figure 12:
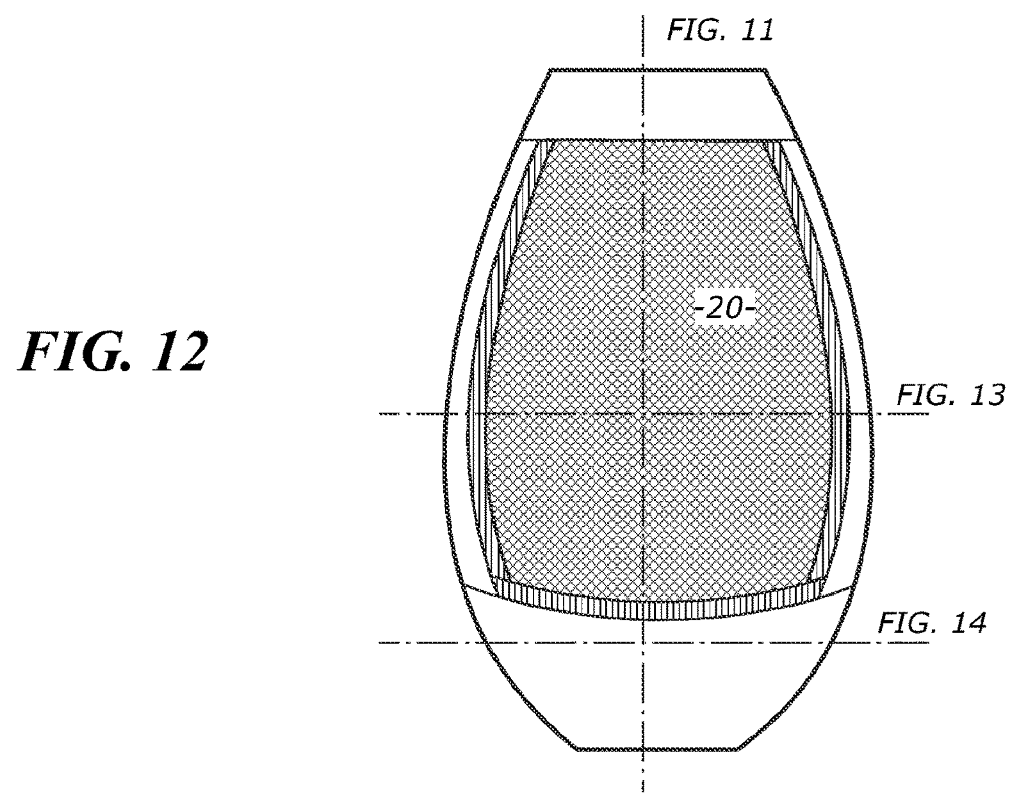
FIG. 12 shows a mens pouch assembly with cut through positions for FIGS. 11, 13 and 14
Figure 13:
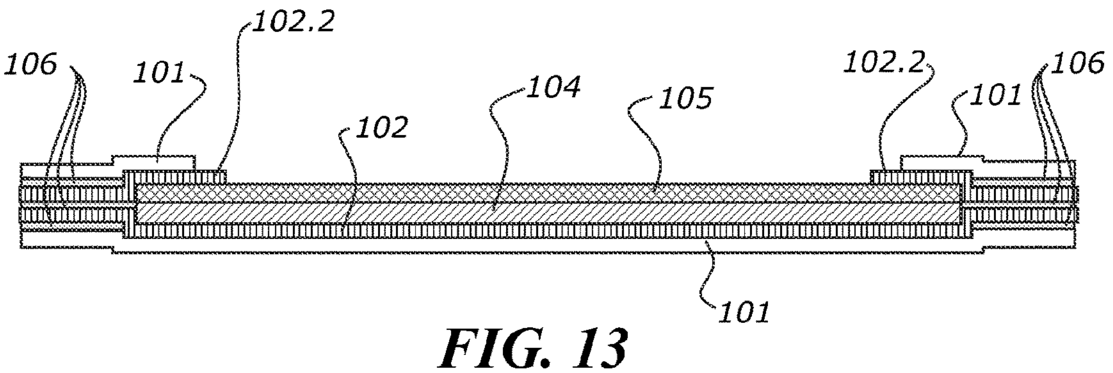
FIG. 13 shows a cut through view of the mens pouch assembly at the higher moisture absorbing section—the first point of mens genital discharge
Figure 14:
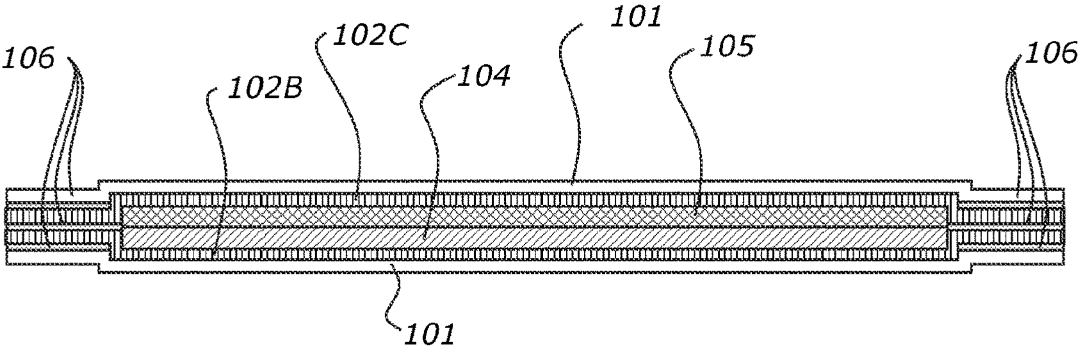
FIG. 14 shows a cut through view of the mens pouch assembly at the lower section that is fully leakproof all around and is the gravity moisture collection pocket that collects all moisture and retains it within the moisture collection pocket.

FIG. 11 represents a cut through view the mens pouch/incontinence pouch for men with a moisture collection pocket where in the same components of the same material may be present in the same configuration except for the foam layer not being present. FIG. 12 shows a rear view (looking onto the inner side) of the men's pouch. FIG. 13 shows a cut through view of the mens pouch assembly at the higher moisture absorbing section—the first point of mens genital discharge. FIG. 14 shows a cut through view of the mens pouch assembly at the lower section that is fully leakproof all around and is the gravity moisture collection pocket that collects all moisture and retains it within the moisture collection pocket. The moisture may be genital discharge and/or other moisture from genital area of the person.

Figure 15:
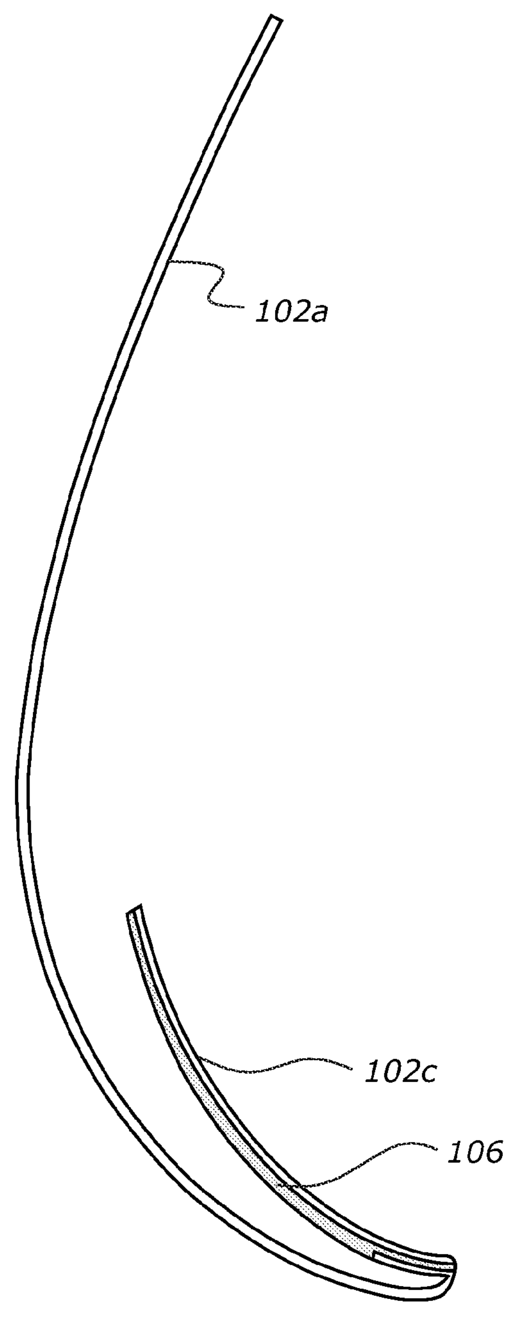
FIG. 15 shows a cut through view of the leakproof layer of the mens pouch assembly.
Figure 16:
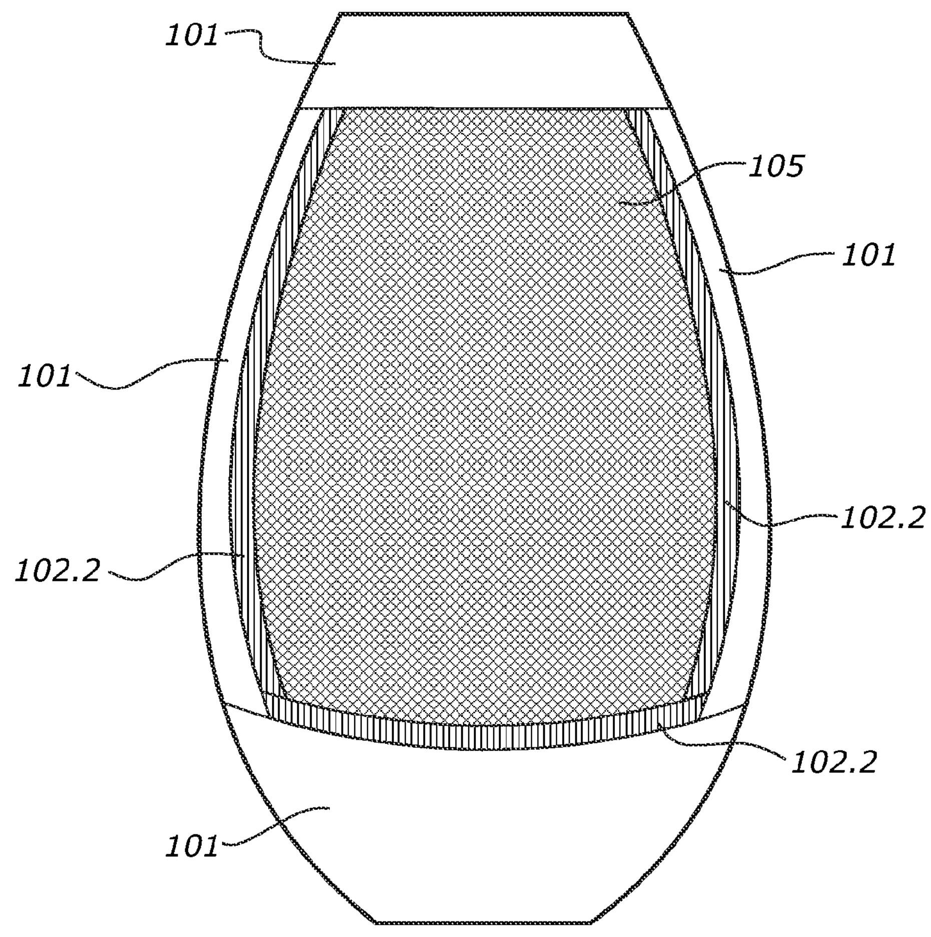
FIG. 16 shows a design option for the mens pouch assembly with gravity moisture collection pocket but is not limited to this current design option.
Figure 17:
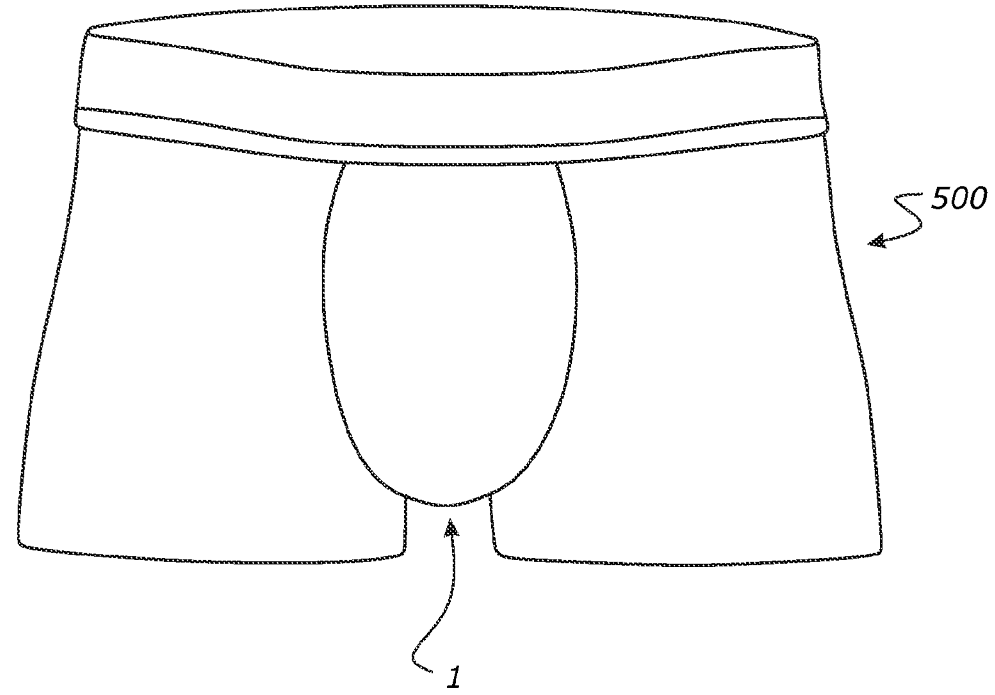
FIG. 17 is a front view of an undergarment in the form of underpants that include or can incorporate the article of the present invention.

FIG. 15 shows a cut through view of the leakproof layer of the mens pouch assembly and FIG. 16 shows a design option for the mens pouch assembly with gravity moisture collection pocket but is not limited to this current design option. In the mens pouch no opening to insert a man's genitalia is provided for. The pouch can collect moisture and absorb it and pool it in the pocket without the need for the genitalia to be inserted.

In the preferred form of the invention the leakproof layer is provided around all sided of the pad or pouch and in a sealing manner. This helps trap moisture in the pad/pouch. The present invention helps to fully trap the moisture on the way down to the pocket and helps prevent leakage at the bottom of the nurse pads or in case of male underwear it does not reach the narrowest part of the crotch and moisture is therefore contained there avoiding the risk of leakage in the most sensitive parts of the product. The article is able to be washed and dried for re-use. Alternatively, the article may be a disposable one-time use article.

The invention claimed is:

1. A reusable moisture retaining article of or for use with an undergarment to be positioned adjacent a person's body and to receive moisture from a person wearing the article, the article comprising:

a leakproof layer formed or assembled to define, at an upper region of the article, an outer layer of the article and, at a lower region of the article, an outer layer and an inner layer of the article;

a leakproof pocket formed between the inner layer and the outer layer at the lower region to allow moisture received from the person, to drain under gravity into the leakproof pocket and be retained in the leakproof pocket when the article is in its upright condition with the upper region above the lower region;

a window region to receive the moisture from the person defined at an inner side of the article;

a core for transferring the moisture therethrough is laminated or otherwise bonded to and between the outer layer and the inner layer, the outer layer being the outer layer at at least one of the upper region and the lower region, wherein a portion of the outer layer overlaps with, and is bonded to, a portion of the inner layer, wherein said portion of the outer layer is between the core and the inner layer at the lower region, and wherein the core comprises a wicking layer positioned toward the inner layer and a moisture absorbing layer positioned away from the inner layer, wherein the moisture absorbing layer is adjacent and bonded to the wicking layer wherein the wicking layer is presented for contact with the person's body; and wherein the article is reusable through washing.

2. The reusable moisture retaining article as claimed in claim 1 wherein the article is positioned to receive moisture from the person from above the leakproof pocket, or with the inner layer most proximate the person than the outer layer at the lower region.

3. The reusable moisture retaining article as claimed in claim 1 wherein the leakproof layer extends downwardly from the upper region to the bottom of the lower region at its outer layer and extends upwardly from the bottom of the lower region to the top of the lower region at its inner layer, the leakproof layer extends downwardly from the top of the upper region to the bottom of the lower region at its outer layer and extends upwardly from the bottom of the lower region to the top of the lower region at its inner layer, the leakproof layer extends downwardly from the top of the upper region to the bottom of the lower region at its outer layer and extends upwardly from the bottom of the lower region no higher than the top of the lower region at its inner layer, or the window is defined between the top of the leakproof layer at the inner layer and the top of the leakproof layer at the top of the outer layer at the upper region.

4. The reusable moisture retaining article as claimed in claim 1 wherein a mouth entrance to the leakproof pocket is defined between the top of the leakproof layer at the inner layer and the outer layer at the lower region.

5. The reusable moisture retaining article as claimed in claim 4 wherein the mouth entrance is the only opening to the leakproof pocket.

6. The reusable moisture retaining article as claimed in claim 5 wherein the mouth entrance is the upper most part of the leakproof pocket.

7. The reusable moisture retaining article as claimed in claim 4 wherein the leakproof pocket is defined by the outer layer and inner layer of the leakproof layer peripherally bonded to each other save for at the mouth entrance.

8. The reusable moisture retaining article as claimed in claim 1 wherein an outer most layer is located outwardly of the outer layer at at least one of the upper and lower region.

9. The reusable moisture retaining article as claimed in claim 8 wherein the outer most layer is the outer most layer of the article, a decorative layer of the article, a protective layer to the outer layer at at least one of the upper and lower regions, laminated or otherwise bonded to the outer layer at at least one of the upper and lower regions, coextensive with the outer layer at at least one of the upper and lower regions, or extends from the top of the article to the bottom of the article.

10. The moisture retaining article as claimed in claim 1 wherein an inner most layer is located outwardly of the inner layer, an inner most layer of the article, a decorative layer of the article, a protective layer to the inner layer, is laminated or otherwise bonded to the inner layer, coextensive with the inner layer, extends from the top of the lower region of article to the bottom of the article, or extends from a mouth entrance of the leakproof pocket to the bottom of the article.

11. The reusable moisture retaining article as claimed in claim 1 wherein the core is located at least in the leakproof pocket, the leakproof pocket is filled with the core, the core is located to inside of the outer layer at at least one of the upper and lower regions, or the core is located to outside of the inner layer.

12. The reusable moisture retaining article as claimed in claim 1 wherein the core further comprises a foam layer.

13. The reusable moisture retaining article as claimed in claim 12 wherein the foam layer is located adjacent the moisture absorbing layer and is laminated or otherwise bonded to the moisture absorbing layer, extends from the top of the article to the bottom of the article and is located in the leakproof pocket, is shaped in thickness, or is of uneven thickness.

14. The reusable moisture retaining article as claimed in claim 12 wherein the moisture absorbing layer is shaped in thickness.

15. The reusable moisture retaining article as claimed in claim 12 wherein the moisture absorbing layer is of uneven thickness.

16. The reusable moisture retaining article as claimed in claim 1 wherein the wicking layer is the inner most layer at the upper region of the article, is presented for contact with the wearer, extends from the top of the article to the bottom of the article and is located in the leakproof pocket, or extends from the top of the article to the bottom of the article and is located in the leakproof pocket where it is laminated or otherwise bonded to the inner layer.

17. The reusable moisture retaining article as claimed in claim 1 wherein the moisture absorbing layer is located adjacent the wicking layer and is laminated or otherwise bonded to the wicking layer, is located adjacent the wicking layer and is laminated or otherwise bonded to the outer layer at at least one of the upper and lower region, is located adjacent the wicking layer and is laminated or otherwise bonded to the wicking layer and is laminated or otherwise bonded to the outer layer at at least one of the upper and lower region, or extends from the top of the article to the bottom of the article and in the leakproof pocket.

18. The reusable moisture retaining article as claimed in claim 1 presented as a multilayer assembly, presented as a multilayer assembly of laminated layers of material, presented as a pad of a multilayer assembly, or being of a contoured shape.

19. The garment that includes said article of claim 1.

20. The garment that is able to receive the article of claim 1 in a dedicated location of the garment.

* * * * *